US012043910B2

(12) United States Patent
Kim et al.

(10) Patent No.: US 12,043,910 B2
(45) Date of Patent: Jul. 23, 2024

(54) INTEGRATED SYSTEM COMPRISING ELECTROCATALYSIS DEVICE OF GLYCEROL AND CHEMICAL CATALYSIS DEVICE OF BIOMASS

(71) Applicant: Korea Research Institute of Chemical Technology, Daejeon (KR)

(72) Inventors: Hyung Ju Kim, Sejong (KR); Jeehoon Han, Jeonju-si (KR); Ho Jeong Chae, Sejong (KR); Jeong-Rang Kim, Daejeon (KR); Soon Yong Jeong, Daejeon (KR); Beom Sik Kim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 1151 days.

(21) Appl. No.: 16/088,353

(22) PCT Filed: Jul. 11, 2017

(86) PCT No.: PCT/KR2017/007404
§ 371 (c)(1),
(2) Date: Sep. 25, 2018

(87) PCT Pub. No.: WO2018/012847
PCT Pub. Date: Jan. 18, 2018

(65) Prior Publication Data
US 2020/0399767 A1 Dec. 24, 2020

(30) Foreign Application Priority Data

Jul. 14, 2016 (KR) .................. 10-2016-0089469

(51) Int. Cl.
*C25B 3/23* (2021.01)
*C07C 51/42* (2006.01)
(Continued)

(52) U.S. Cl.
CPC ............... *C25B 3/23* (2021.01); *C07C 51/42* (2013.01); *C07H 1/08* (2013.01); *C25B 1/02* (2013.01);
(Continued)

(58) Field of Classification Search
CPC .... C25B 1/02; C25B 3/07; C25B 3/23; C25B 15/08; C25B 15/081; C25B 2/07; C25B 2/23; C07C 51/42
See application file for complete search history.

(56) References Cited

U.S. PATENT DOCUMENTS

| 7,145,049 B2 | 12/2006 | Loescher et al. | |
|---|---|---|---|
| 2015/0159285 A1* | 6/2015 | Baldauf | C22B 26/00 205/560 |
| 2017/0121832 A1* | 5/2017 | Albrecht | C25B 15/081 |

FOREIGN PATENT DOCUMENTS

| KR | 10-2007-0095176 | 9/2007 | |
|---|---|---|---|
| WO | WO-2009145624 A1 * | 12/2009 | ............... C25B 3/02 |

OTHER PUBLICATIONS

Kim, H.J., Lee, J., Green, S.K., Huber, G.W. and Kim, W.B. (2014), Selective Glycerol Oxidation by Electrocatalytic Dehydrogenation. ChemSusChem, 7: 1051-1056. (Year: 2014).*

(Continued)

*Primary Examiner* — Luan V Van
*Assistant Examiner* — Mofoluwaso S Jebutu
(74) *Attorney, Agent, or Firm* — DeWitt LLP

(57) ABSTRACT

The present invention provides an integrated system comprising: an electrocatalysis device, in which an oxidation reaction is carried out at an anode by an electrocatalysis of glycerol, and at a cathode hydrogen is produced through a reduction reaction; and a chemical catalysis device for producing butene oligomers from lignocellulosic biomass through a hydrogenation process, wherein the hydrogen produced by the electrocatalysis device is used for the
(Continued)

production of the butene oligomers by the chemical catalysis device, and a thermal energy of the electrocatalysis device and the chemical catalysis device is exchanged with each other. The integrated system according to the present invention can reduce the cost of materials of a process for preparing butene oligomers by using hydrogen, which is a byproduct of a process for preparing glycerol derivatives, as a material of a process for preparing the butene oligomers through the integration of materials and energy from the processes for preparing glycerol derivatives and butene oligomers, and can obtain an effect of reducing energy costs by greatly reducing energy required in an integrated process by supplying, as a part of a thermal energy required at the process for preparing glycerol derivatives, the waste heat of the process for preparing the butene oligomers through the construction of a thermal energy integration network.

7 Claims, 6 Drawing Sheets

(51) Int. Cl.
   C07H 1/08        (2006.01)
   C25B 1/02        (2006.01)
   C25B 3/07        (2021.01)
   C25B 9/19        (2021.01)
   C25B 15/08       (2006.01)
(52) U.S. Cl.
   CPC .................. *C25B 3/07* (2021.01); *C25B 9/19* (2021.01); *C25B 15/08* (2013.01); *C25B 15/081* (2021.01)

(56) References Cited

OTHER PUBLICATIONS

Jeehoon Han, S. Murat Sen, David Martin Alonso, James A. Dumesica and Christos T. Maravelias, Green Chem., 2014, 16, 653-661 (Year: 2014).*

S. Murat Sen, David Martin Alonso, Stephanie G. Wettstein, Elif I. Gürbüz, Carlos A. Henao, James A. Dumesic and Christos T. Maravelias, Energy Environ. Sci., 2012, 5, 9690-9697 (Year: 2012).*
Shah, V.H. and Agrawal, R. (2010), A matrix method for multicomponent distillation sequences. AIChE J., 56: 1759-1775. (Year: 2010).*
Jeehoon Han, S. Murat Sen, David Martin Alonso, James A. Dumesic and Christos T. Maravelias, Supplementary Information of "A strategy for the simultaneous catalytic conversion of hemicellulose and cellulose from lignocellulosic biomass to liquid transportation fuels", Green Chem., 2014,16, 653-661 (Year: 2014).*
Pierre Gallezot, "Selective oxidation with air on metal catalysts", 37 Catalysis Today, pp. 405-418 (Elsevier Science B.V. 1997).
Seonhwa Lee, et al., "Highly selective transformation of glycerol to dihydroxyacetone without using oxidants by a PtSb/C-catalyzed electronoxidation process", 18 Green Chemistry, pp. 2877-2887 (Royal Society of Chemistry 2016).
Byun, Jaewon; Han, Jeehoon, "Techno economic feasiblity study for catalytic butene oligomers production from lignocellulosic biomass using 2-sec-butylphenol solvents", pp. 1226-1231 (12th International Conference on Heat Transfer, Fluid Mechanics and Thrmodynamics—Costa de Sol, Spain, Jul. 11-13, 2016).
S. Murat Sen, et al., "Production of Butene Oligomers as Transportation Fuels using Butene for Esterification of Levulinic Acid from Lignocellulosic Biomass: Process Synthesis and Technoeconomic Evaluation", Green Chemistry, pp. 1-12 (RSC Publishing, Oct. 1, 2012).
Zhiyong Zhang, et al., "Electrocatalytic oxidation of glycerol on Pt/C in anion-exchange membrane fuel cell: Cogeneration of electricity and valuable chemicals", 119-120 Applied Catalysis B: Environmental, pp. 40-48 (Elsevier B. V. 2012).
"Chemical catalytic conversion process for production of woody biomass-based butene oligomers and tetrahydrofurfuryl alcohol", Theories and Applications of Chem. Eng., 2016, vol. 22, No. 1.
Hyung Ju Kim, et al., "Selective Glycerol Oxidation by Electrocatalytic Dehydrogenation", ChemSusChem Communications, pp. 1051-1054 (Wiley Online Library 2014).
Hyung Ju Kim, et al., "Coproducing Value-Added Chemicals and Hydrogen with Electrocatalytic Glycerol Oxidation Technology: Experimental and Techno-Economic Investigations", ACS Sustainable Chemistry & Engineering, pp. 6626-6634 (ACSPublications 2017).

* cited by examiner

INTEGRATED SYSTEM COMPRISING ELECTROCATALYSIS DEVICE OF GLYCEROL AND CHEMICAL CATALYSIS DEVICE OF BIOMASS

TECHNICAL FIELD

The present invention relates to an integrated system, which comprises: an electrocatalytic conversion process for the low-cost production of value-added chemicals (glyceraldehyde (GAD), glyceric acid (GLA), and hydroxypyruvic acid (HPA)) from glycerol, which is a byproduct of biodiesel production; and a chemical catalytic conversion process from lignocellulosic biomass to a transportation fuel (butene oligomers) using hydrogen, which is a byproduct of the electrocatalytic conversion process, and in which an integrated fusion process of the electrocatalytic-chemical catalytic conversion and a thermal integration network are constructed.

BACKGROUND ART

Recently, many research attempts have been made to produce hydrogen by a method of water electrolysis, as a method for efficiently producing hydrogen. However, the demand for large amounts of electric energy and high overvoltage required for the reaction makes water electrolysis less economically feasible than the conventional fossil fuel based technologies and thus, currently many research attempts have been made to improve related problems.

Recently, development of an electrocatalysis process for utilizing raw materials extracted from biomass so as to efficiently prepare value-added chemicals has been attempted. In particular, glycerol is produced as an important byproduct in the biodiesel production process.

The oxidation of glycerol can be used to produce chemicals such as glyceraldehyde (GAD), glyceric acid (GLA), and hydroxypyruvic acid (HPA). Glyceraldehyde, one of the chemicals produced by the reaction, can be used as a component of cosmetics, and further oxidation of glyceraldehyde produces carboxylic acids such as glyceric acid. These carboxylic acids can be converted into various products such as polymers, and currently these kinds of acid materials have a limited market since there are restrictions on mass production due to expensive synthesis processes and methods. Therefore, there is an urgent need to develop methods for efficiently and cheaply producing chemicals such as acids by selective oxidation of glycerol.

The oxidation of glycerol has been mostly investigated using pressurized oxygen as an oxidant in heterogeneous catalysis. The catalytic glycerol oxidation results in different product selectivity, depending on various reaction conditions such as reaction temperatures, oxygen pressure, pH, the ratio of glycerol/catalyst, and catalysts used (Au, Pt, Pd, AuPt, AuPd, and so on). While mainly materials such as glyceric acid, glyceraldehyde, and dihydroxyacetone have been reported as selective oxidation products of glycerol, there is a drawback that the yields of products are not good due to the problem that the selectivity decreases as the conversion increases (Catal. Today, 37, 405, 1997).

As for electrocatalytic oxidation technology, the pressurized oxygen, which is used as an oxidant in the conventional heterogeneous catalytic oxidation, is not required, and the reaction takes place by controlling potential of the catalytic electrode and produces hydrogen as a byproduct of the reaction at the same time.

As for the reaction principle, the electrocatalytic oxidation of glycerol produces glyceraldehyde, hydrogen ions, and electrons at an anode, and the resulting hydrogen ions transfer to a cathode, through a liquid electrolyte in an electrocatalytic batch reactor and through a solid polymer electrolyte in an electrocatalytic continuous-flow reactor, respectively. At the cathode, hydrogen ions transferred through the electrolytes combine with electrons moved along the outer conductive wire to form hydrogen. The reactions in the electrocatalytic reactor using Pt/C catalyst are as shown in the following Reaction formula 1:

Anode reaction: $C_3H_8O_3 \rightarrow C_3H_6O_3 + 2H^+ + 2e^-$

Cathode reaction: $2H^+ + 2e^- \rightarrow H_2$

Overall reaction: $C_3H_8O_3 \rightarrow C_3H_6O_3 + H_2$ <Reaction formula 1>

Meanwhile, butene oligomers are produced through the chemical catalytic conversion process of lignocellulosic biomass. Celluloses and hemicelluloses of lignocellulosic biomass are converted to furfural (FF) and levulinic acid (LA) under sulfuric acid catalyst, and subsequently, furfural (FF) is converted to levulinic acid (LA) via furfuryl alcohol under $Pt_3Sn/SiO_2$ catalyst and Amberlyst 70 catalyst. Levulinic acid (LA) is converted to gamma-valerolactone (GVL) under $RuSn_4/C$ catalyst, and finally converted to butene oligomers via butene under $SiO_2/Al_2O_3$ and Amberlyst 70 catalysts.

These conversions have problems of requiring, as a reactant, hydrogen and large amounts of cooling energy due to an exothermic reaction and a condensation process. Hydrogen produced based on the conventional fossil fuels is currently used as the hydrogen required for the production of fuels such as butene oligomers from biomass, and one of the main problems in using these hydrogenation technologies is that the presently used hydrogenation technology requires a large amount of hydrogen (0.034 kg hydrogen per kg of feedstock). In addition, the price of hydrogen required for hydrogenation technology is equivalent to or higher than that of biomass and varies depending on the location or distance. For example, the price of hydrogen is low ($1 per kg) near a petroleum refinery, but is approximately two times expensive in the area away from the refinery (for example, the area rich in biomass resources) due to the expenses of storage and transportation. Accordingly, there is an urgent need for a method for efficiently producing hydrogen at a low cost in order to produce renewable fuels and chemicals in a cost-effective way by using biomass hydrogenation technology.

DISCLOSURE OF THE INVENTION

Technical Problem

Therefore, it is an object of the present invention to provide an integrated system in which materials and energy generated upon preparation of glycerol derivatives and butene oligomers are exchanged through the fusion of an electrocatalysis device and a chemical catalysis device, in which the electrocatalysis device carries out electrocatalysis which produces glycerol derivatives and hydrogen from glycerol, which is a byproduct of biodiesel production, and the chemical catalysis device produces butene oligomers from lignocellulosic biomass through a hydrogenation process.

Technical Solution

In order to accomplish the above object, the present invention provides an integrated system, comprising:
an electrocatalysis device, in which an oxidation reaction is carried out at an anode by an electrocatalysis of glycerol, and at a cathode hydrogen is produced through a reduction reaction; and
a chemical catalysis device for producing butene oligomers from lignocellulosic biomass through a hydrogenation process,
wherein the hydrogen produced by the electrocatalysis device is used for the production of butene oligomers by the chemical catalysis device, and the thermal energy of the electrocatalysis device and the chemical catalysis device is exchanged with each other.

The present invention also provides an integrated system, comprising:
an electrocatalysis device, comprising: a reaction unit which comprises an anode, a cathode, and an electrolyte; and a purification unit for purifying a reaction product produced by the reaction unit, in which an oxidation reaction is carried out at the anode by an electrocatalysis of glycerol, and at the cathode hydrogen is produced through a reduction reaction; and
a chemical catalysis device for producing butene oligomers from lignocellulosic biomass through a hydrogenation process, the chemical catalysis device comprising: a first hydrolysis unit for hydrolyzing lignocellulosic biomass so as to produce a first hydrolysate; a first hydrogen reaction unit for subjecting the first hydrolysate produced by the first hydrolysis unit to a reaction with hydrogen so as to produce a first hydrogen reactant; a second hydrolysis unit for hydrolyzing the first hydrogen reactant produced by the first hydrogen reaction unit so as to produce a second hydrolysate; a second hydrogen reaction unit for subjecting the second hydrolysate produced by the second hydrolysis unit to a reaction with hydrogen so as to produce a second hydrogen reactant; a hydrogen reactant purification unit for purifying the second hydrogen reactant produced by the second hydrogen reaction unit; a butene preparation unit for catalyzing the second hydrogen reactant purified by the hydrogen reactant purification unit so as to prepare a butene mixture comprising butene; and a butene oligomer preparation unit for preparing butene oligomers from the butene mixture prepared by the butene preparation unit,
wherein the hydrogen produced by the reaction unit in the electrocatalysis device is supplied to the first hydrogen reaction unit and the second hydrogen reaction unit, and
the thermal energy of the electrocatalysis device and the chemical catalysis device is exchanged with each other.

Further, the present invention provides a method comprising:
a step of carrying out an oxidation reaction at an anode by an electrocatalysis of glycerol and at a cathode producing hydrogen through a reduction reaction (step 1-1);
a step of purifying one or more value-added chemicals selected from the group consisting of glyceraldehyde (GAD), hydroxypyruvic acid (HPA), and glyceric acid (GLA) from the reaction products produced through the oxidation reaction at the anode in step 1-1 (step 1-2);
a step of hydrolyzing lignocellulosic biomass to furfural (FF) and levulinic acid (LA) (step 2-1);
a step of subjecting furfural (FF) produced in step 2-1 to a reaction with hydrogen so as to convert to furfuryl alcohol (FFA) (step 2-2);
a step of hydrolyzing furfuryl alcohol (FFA) produced in step 2-2 to levulinic acid (LA) (step 2-3);
a step of subjecting levulinic acid (LA) to a reaction with hydrogen so as to convert to gamma-valerolactone (GVL) (step 2-4); and
a step of producing butene oligomers from gamma-valerolactone (GVL) produced in step 2-4 (step 2-5),
wherein hydrogen produced in step 1-1 is used for step 2-2 and step 2-4, and the steps exchange the thermal energy with one another.

Advantageous Effects

The integrated system according to the present invention can reduce the cost of raw materials of a process for preparing butene oligomers by using hydrogen, which is a byproduct of a process for preparing glycerol derivatives, as a raw material of a process for preparing butene oligomers through the integration of materials and energy from the processes for preparing glycerol derivatives and butene oligomers, and can obtain an effect of reducing energy costs by greatly reducing energy required in the integrated process by supplying, as a part of the thermal energy required at the process for preparing glycerol derivatives, the waste heat of the process for preparing butene oligomers through the construction of a thermal energy integration network.

BEST MODE FOR CARRYING OUT THE INVENTION

Figure 1:
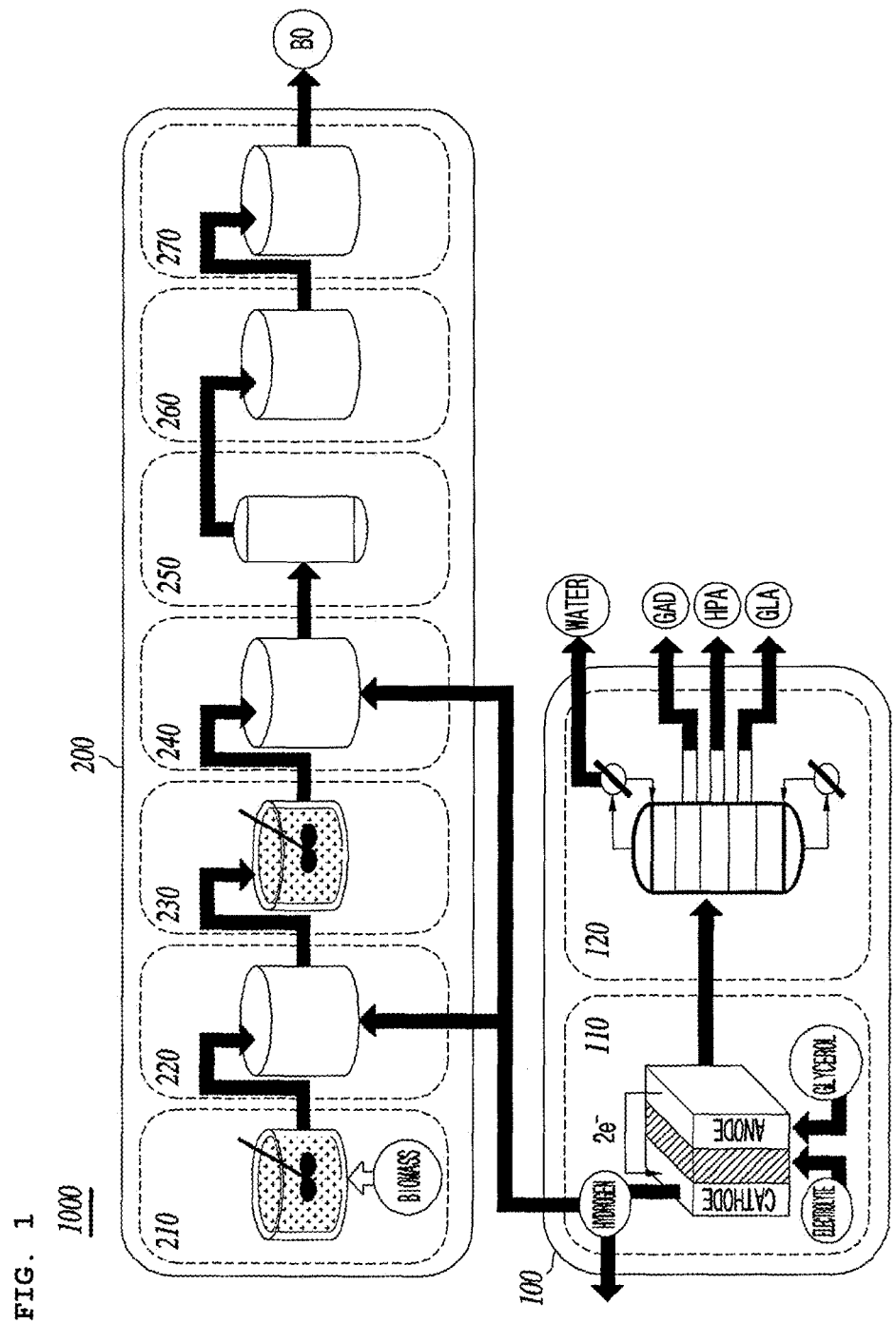
FIG. 1 is a schematic diagram showing one example of an integrated system according to the present invention.

The present invention provides an integrated system, comprising:
an electrocatalysis device, in which an oxidation reaction is carried out at an anode by an electrocatalysis of glycerol, and at a cathode hydrogen is produced through a reduction reaction; and
a chemical catalysis device for producing butene oligomers from lignocellulosic biomass through a hydrogenation process,
wherein the hydrogen produced by the electrocatalysis device is used for the production of the butene oligomers by the chemical catalysis device, and the thermal energy of the electrocatalysis device and the chemical catalysis device is exchanged with each other.

Herein, one example of the integrated system according to the present invention is shown as schematic diagrams in FIGS. 1-4.

Hereinafter, the integrated system according the present invention will now be described in detail with reference to the schematic diagrams shown in FIGS. 1-4.

The integrated system 1000 according to the present invention comprises: the electrocatalysis device 100, in which the oxidation reaction is carried out at the anode by the electrocatalysis of glycerol, and at the cathode hydrogen is produced through the reduction reaction; and the chemical catalysis device 200 for producing butene oligomers from lignocellulosic biomass through a hydrogenation process, and is characterized in that the hydrogen produced by the electrocatalysis device is used for the production of butene oligomers by the chemical catalysis device, and the thermal energy of the electrocatalysis device and the chemical catalysis device is exchanged with each other.

The integrated system 1000 is characterized in that high-purity hydrogen, i.e. the hydrogen of high purity and with no separate purification process required, produced through the electrocatalysis of glycerol, which is a byproduct of biodiesel production, is applied to a process requiring hydrogen in a conversion process of biomass. The hydrogen thus produced through the electrocatalysis of glycerol is of high purity, without additional separation or purification processes, and can be supplied efficiently and directly to the conversion process of biomass so as to reduce the cost of materials.

In addition, the efficiency of the integrated system can be maximized by lowering a large amount of separation energy required in the electrochemical process through heat exchange between reaction devices in which two types of processes are performed.

In the integrated system 1000 according to the present invention, the electrocatalysis device 100 produces glycerol derivatives at the anode by the oxidation reaction through the electrocatalysis of glycerol, and produces hydrogen at the cathode by the reduction reaction.

The electrocatalysis device 100 comprises: the reaction unit 110 which comprises the anode, the cathode, and the electrolyte; and the purification unit 120 for purifying a reaction product produced by the reaction unit.

The reaction unit 110 may comprise an electrocatalytic reactor, and may comprise, as a catalyst, Pt/C, Pt, C and the like, but the catalyst is not limited thereto. The electrolyte may be an acid aqueous solution, and may be, but is not limited to, a sulfuric acid aqueous solution.

In the reaction unit, glycerol derivatives may be produced at the anode and hydrogen may be produced at the cathode, as shown in the following reaction formulas 2 and 3:

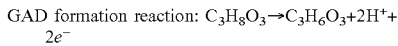

GAD formation reaction: $C_3H_8O_3 \rightarrow C_3H_6O_3 + 2H^+ + 2e^-$

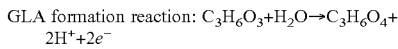

GLA formation reaction: $C_3H_6O_3 + H_2O \rightarrow C_3H_6O_4 + 2H^+ + 2e^-$

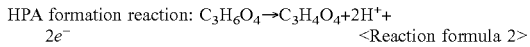

HPA formation reaction: $C_3H_6O_4 \rightarrow C_3H_4O_4 + 2H^+ + 2e^-$ <Reaction formula 2>

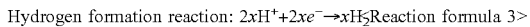

Hydrogen formation reaction: $2xH^+ + 2xe^- \rightarrow xH_2$ <Reaction formula 3>

As in Reaction formula 3, hydrogen is produced in the cathode due to the electrocatalysis in the reaction unit 110 in the electrocatalysis device 100, and the produced hydrogen is one of valuable byproducts of the electrochemical glycerol oxidation reaction.

The present invention applies hydrogen produced by the electrocatalysis device 100 to the biomass hydrogenation process in the chemical catalysis device 200, thereby producing value-added chemicals at the same time, while consuming less electric energy compared to the existing hydrogen production technology, water electrolysis technology, and it has advantages of high yield of chemical products and rapid production speed.

The electrocatalysis device 100 may further comprise a neutralization reaction unit (not shown) for neutralizing the acid aqueous solution used as the electrolyte in the reaction unit 110.

Figure 2:
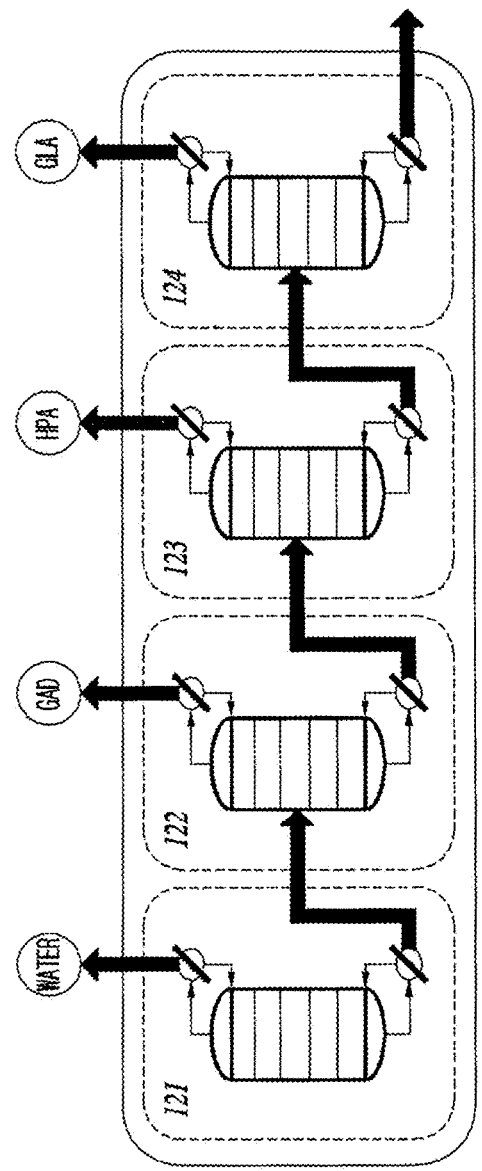
FIG. 2 is a schematic diagram showing one example of a purification unit of the integrated system according to the present invention.

In addition, the purification unit 120, may comprise: the removal unit 121 for removing water and other impurities from the reaction products; the first purification unit 122 for purifying glyceraldehyde (GAD) from the reaction products; the second purification unit 123 for purifying hydroxypyruvic acid (HPA) from the reaction products; and the third purification unit 124 for purifying glyceric acid (GLA) from the reaction products, as shown in FIG. 2.

The purification unit 120 comprises, as device components for purifying glycerol derivatives, which are the reaction products produced from the reaction unit 110: the removal unit 121 for removing water and other impurities; the first purification unit 122 for purifying GAD; the second purification unit 123 for purifying HPA; and the third purification unit 124 for purifying GLA.

The glycerol derivatives are the reaction product produced through the reaction at the anode as shown in Reaction formula 2.

The removal unit 121 for removing water and other impurities may comprise a multi-stage distillation apparatus and the multi-stage distillation apparatus may be a continuous multi-stage distillation apparatus having 8 to 12 stages.

The first purification unit 122 for purifying GAD may comprise a multi-stage distillation apparatus and the multi-stage distillation apparatus may be a multi-stage distillation apparatus having 10 to 16 stages.

The second purification unit 123 for purifying HPA may comprise a multi-stage distillation apparatus and the multi-stage distillation apparatus may be a multi-stage distillation apparatus having 45 to 55 stages.

The third purification unit 124 for purifying GLA may comprise a multi-stage distillation apparatus and the multi-stage distillation apparatus may be a multi-stage distillation apparatus having 35 to 45 stages.

In the integrated system 1000 according to the present invention, the chemical catalysis device 200 may comprise: the first hydrolysis unit 210 for hydrolyzing lignocellulosic biomass so as to produce a first hydrolysate; the first hydrogen reaction unit 220 for subjecting the first hydrolysate produced by the first hydrolysis unit to a reaction with hydrogen so as to produce a first hydrogen reactant; the second hydrolysis unit 230 for hydrolyzing the first hydrogen reactant produced by the first hydrogen reaction unit so as to produce a second hydrolysate; the second hydrogen reaction unit 240 for subjecting the second hydrolysate produced by the second hydrolysis unit to a reaction with hydrogen so as to produce a second hydrogen reactant; the hydrogen reactant purification unit 250 for purifying the second hydrogen reactant produced by the second hydrogen reaction unit; the butene preparation unit 260 for catalyzing the second hydrogen reactant purified by the hydrogen reactant purification unit so as to prepare a butene mixture comprising butene; and the butene oligomer preparation unit 270 for preparing butene oligomers from the butene mixture prepared by the butene preparation unit.

In addition, the chemical catalysis device 200 may further comprise the butene purification unit 280 for purifying the butene mixture prepared by the butene preparation unit 260.

The chemical catalysis device 200 can finally prepare butene oligomers through hydrolysis using a chemical catalyst and the reaction with hydrogen.

In the first hydrolysis unit 210, sulfuric acid may be used as the catalyst, but the catalyst is not limited thereto. The lignocellulosic biomass may be corn stover, wheat straw, hybrid poplar, switchgrass, loblolly pine, aspen wood, celluloses, hemicelluloses, and the like, and in the first hydrolysis unit, the lignocellulosic biomass may be hydrolyzed to produce the first hydrolysate, as shown in Reaction formula 4 below. Herein, the first hydrolysate may be furfural (FF), levulinic acid (LA), and the like.

FF formation reaction: $C_5H_8O_4 \rightarrow C_5H_4O_2 + 2H_2O$

LA formation reaction: $C_6H_{10}O_5 \rightarrow C_5H_5O_3 + CH_2O_2$  <Reaction formula 4>

In the first hydrogen reaction unit 220, $Pt_3Sn/SiO_2$ (platinum and tin supported on silica) may be used as the catalyst, but the catalyst is not limited thereto. In the first hydrogen reaction unit, the first hydrolysate produced by the first hydrolysis unit 210 is subjected to the reaction with hydrogen, as shown in Reaction formula 5 below so as to produce the first hydrogen reactant, wherein the first hydrolysate may be furfural (FF) and the first hydrogen reactant may be furfuryl alcohol (FFA).

FFA formation reaction: $C_5H_4O_2 + H_2 \rightarrow C_5H_6O_2$  <Reaction formula 5>

In the second hydrolysis unit 230, Amberlyst 70 may be used as the catalyst, but the catalyst is not limited thereto. In the second hydrolysis unit, the first hydrogen reactant produced by the first hydrogen reaction unit 220 is hydrolyzed to produce a second hydrolysate, as shown in Reaction formula 6 below, wherein the first hydrogen reactant may be furfuryl alcohol (FFA) and the second hydrolysate may be levulinic acid (LA).

LA formation reaction: $C_5H_6O_2 + H_2O \rightarrow C_5H_5O_3$  <Reaction formula 6>

In the second hydrogen reaction unit 240, $RuSn_4/C$ (ruthenium and tin supported on carbon) may be used as the catalyst, but the catalyst is not limited thereto. In the second hydrogen reaction unit, the second hydrolysate produced by the second hydrolysis unit 230 is subjected to the reaction with hydrogen so as to produce a second hydrogen reactant, as shown in Reaction formula 7 below, wherein the second hydrolysate may be levulinic acid (LA) and the second hydrogen reactant may be gamma-valerolactone (GVL).

GVL formation reaction: $C_5H_8O_3 + H_2 \rightarrow O_5H_8O_2 + H_2O$  <Reaction formula 7>

The hydrogen reactant purification unit 250 may comprise, as a device component for purifying the hydrogen reactant GVL, which is the raw material for butene oligomers to be obtained by the chemical catalysis device, an evaporator. Also, it may further comprise a separator for separating GVL from impurities such as carbon dioxide and the like.

In the butene preparation unit 260, $SiO_2/Al_2O_3$ may be used as the catalyst, but the catalyst is not limited thereto. In the butene preparation unit, the second hydrogen reactant purified by the hydrogen reactant purification unit 250 is reacted as shown in Reaction formula 8 below so as to prepare a butene mixture comprising butene, wherein the second hydrogen reactant may be gamma-valerolactone (GVL).

Butene formation reaction: $C_5H_8O_2 \rightarrow C_4H_8 + CO_2$  <Reaction formula 8>

In the butene oligomer preparation unit 270, Amberlyst 70 may be used as the catalyst, but the catalyst is not limited thereto. In the butene oligomer preparation unit, butene and the mixture thereof prepared by the butene preparation unit 260 may be reacted to convert to butene oligomers, as shown in Reaction formula 9 below:

$2C_4H_8 \rightarrow C_8H_{16}$ $3C_4H_8 \rightarrow C_{12}H_{24}$ $4C_4H_8 \rightarrow C_{16}H_{32}$ $5C_4H_8 \rightarrow C_{20}H_{40}$  <Reaction formula 9>

Herein, in the butene purification unit 280, the butene mixture prepared by the butene preparation unit 270 may be purified so as to produce pure butene and the butene purification unit for purifying the butene mixture may comprise a multi-stage distillation apparatus and the multi-stage distillation apparatus may be a multi-stage distillation apparatus having 40 to 45 stages.

Figure 3:
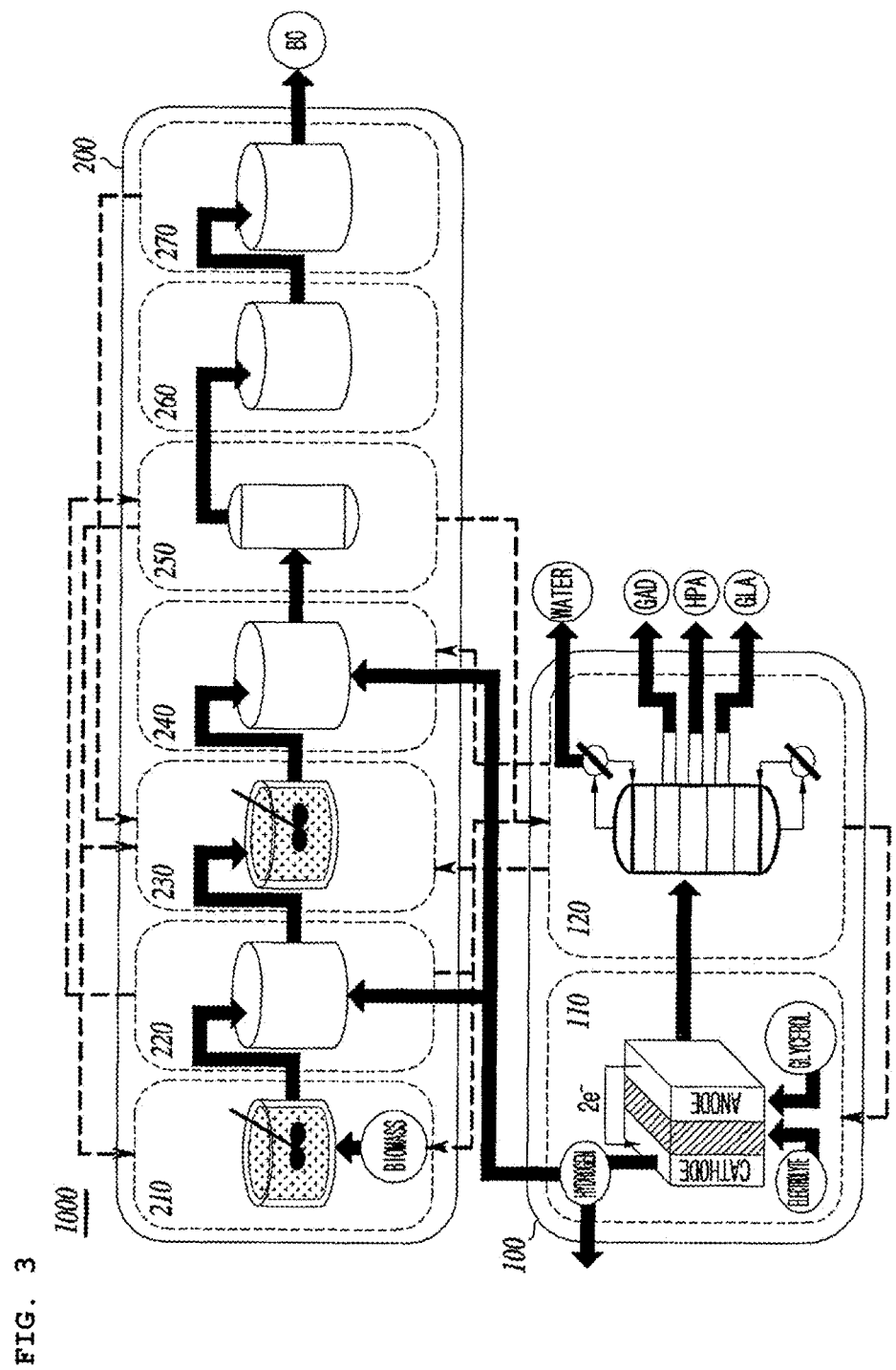
FIGS. 3 and 4 are schematic diagrams showing specifically a thermal integration network according to the present invention.

As shown in FIGS. 1 and 3 as a particular example, the integrated system 1000 according to the present invention comprises:

the electrocatalysis device 100, comprising: the reaction unit 110 which comprises the anode, the cathode, and the electrolyte; and the purification unit 120 for purifying a reaction product produced by the reaction unit, in which an oxidation reaction is carried out at the anode by an electrocatalysis of glycerol, and at the cathode hydrogen is produced through a reduction reaction; and the chemical catalysis device 200 for producing butene oligomers from lignocellulosic biomass through a hydrogenation process, in which the chemical catalysis device comprises: the first hydrolysis unit 210 for hydrolyzing lignocellulosic biomass so as to produce a first hydrolysate; the first hydrogen reaction unit 220 for subjecting the first hydrolysate produced by the first hydrolysis unit to a reaction with hydrogen so as to produce a first hydrogen reactant; the second hydrolysis unit 230 for hydrolyzing the first hydrogen reactant produced by the first hydrogen reaction unit so as to produce a second hydrolysate; the second hydrogen reaction unit 240 for subjecting the second hydrolysate produced by the second hydrolysis unit to a reaction with hydrogen so as to produce a second hydrogen reactant; the hydrogen reactant purification unit 250 for purifying the second hydrogen reactant produced by the second hydrogen reaction unit; the butene preparation unit 260 for catalyzing the second hydrogen reactant purified by the hydrogen reactant purification unit so as to prepare a butene mixture comprising butene; and the butene oligomer preparation unit 270 for preparing butene oligomers from the butene mixture prepared by the butene preparation unit, wherein the hydrogen produced by the reaction unit in the electrocatalysis device is supplied to the first hydrogen reaction unit and the second hydrogen reaction unit, and the thermal energy of the electrocatalysis device and the chemical catalysis device is exchanged with each other.

The integrated system 1000 according to the present invention can reduce energy costs by greatly reducing energy requirement by supplying the electrocatalysis device with a part of the thermal energy required by the electrocatalysis device from the chemical catalysis device through the construction of the thermal energy integration network.

The thermal energy flow in the integrated system 1000 according to the present invention as shown in FIG. 3 is illustrated specifically and will be explained in detail.

The thermal energy required by the reaction unit 110 may be supplied from the purification unit 120.

The thermal energy required by the purification unit 120 may be supplied from one or more units of the first hydrolysis unit 210, the first hydrogen reaction unit 220, and the hydrogen reactant purification unit 250.

The thermal energy required by the first hydrolysis unit 210 may be supplied from one or more units of the purification unit 120 and the hydrogen reactant purification unit 250.

The thermal energy required by the second hydrolysis unit 230 may be supplied from one or more unit of the purification unit 120, the hydrogen reactant purification unit 250, and the butene oligomer preparation unit 270.

The thermal energy required by the hydrogen reactant purification unit 250 may be supplied from the first hydrogen reaction unit 220.

Figure 4:
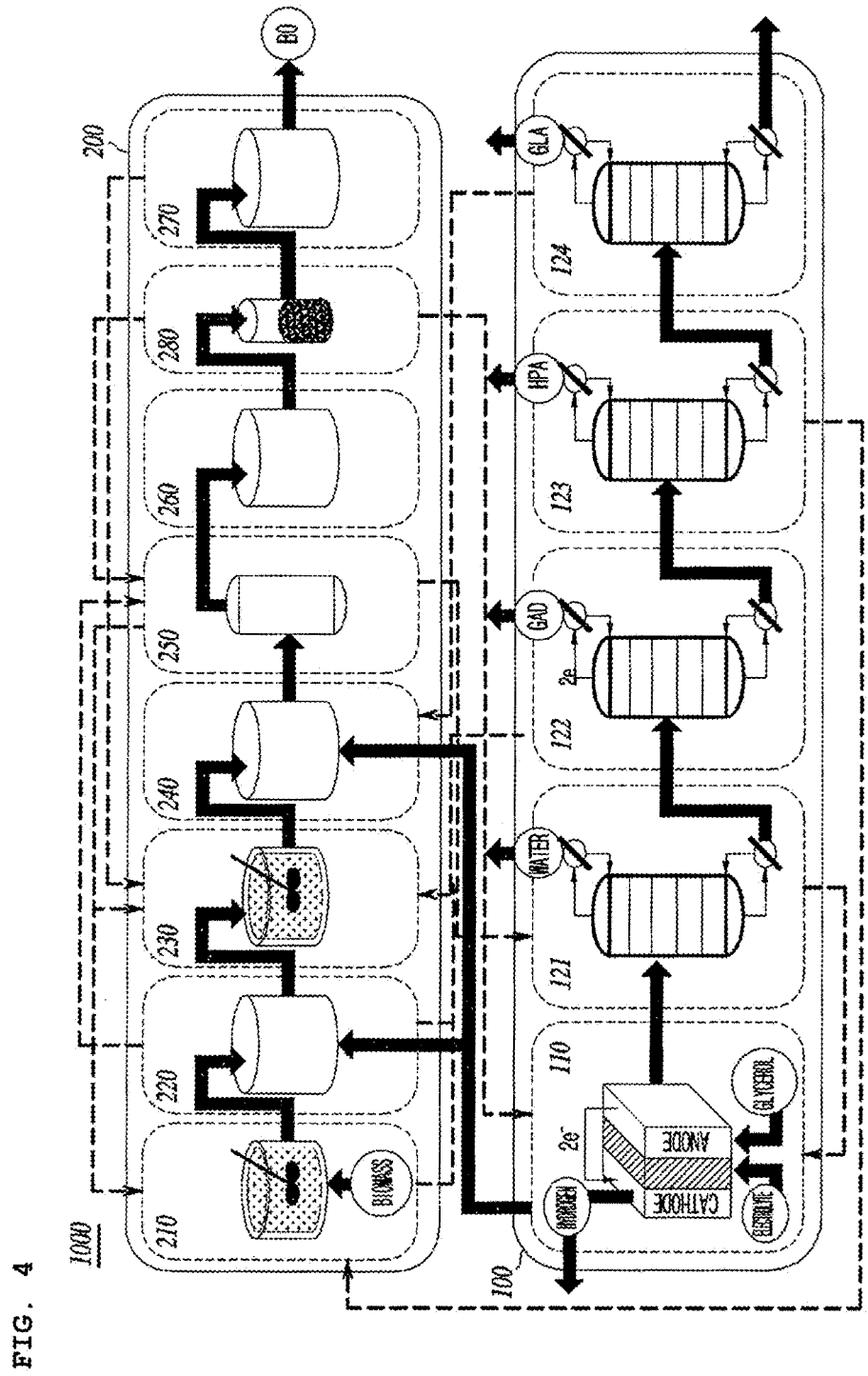

Further, more particularly, the integrated system 1000 according to the present invention comprises, as shown in FIG. 4, the electrocatalysis device 100, comprising: the reaction unit 110 which comprises the anode, the cathode, and the electrolyte; the removal unit 121 for removing water and other impurities from the reaction products produced by the reaction unit; the first purification unit 122 for purifying glyceraldehyde (GAD) from the reaction products passed through the removal unit; the second purification unit 123 for purifying hydroxypyruvic acid (HPA) from the reaction products passed through the first purification unit; and the third purification unit 124 for purifying glyceric acid (GLA) from the reaction products passed through the second purification unit, in which the oxidation reaction is carried out at the anode by the electrocatalysis of glycerol, and at the cathode hydrogen is produced through the reduction reaction; and the chemical catalysis device 200 for producing butene oligomers from lignocellulosic biomass through a hydrogenation process, in which the chemical catalysis device comprises: the first hydrolysis unit 210 for hydrolyzing lignocellulosic biomass so as to produce a first hydrolysate; the first hydrogen reaction unit 220 for subjecting the first hydrolysate produced by the first hydrolysis unit to a reaction with hydrogen so as to produce a first hydrogen reactant; the second hydrolysis unit 230 for hydrolyzing the first hydrogen reactant produced by the first hydrogen reaction unit so as to produce a second hydrolysate; the second hydrogen reaction unit 240 for subjecting the second hydrolysate produced by the second hydrolysis unit to a reaction with hydrogen so as to produce a second hydrogen reactant; the hydrogen reactant purification unit 250 for purifying the second hydrogen reactant produced by the second hydrogen reaction unit; the butene preparation unit 260 for catalyzing the second hydrogen reactant purified by the hydrogen reactant purification unit so as to prepare a butene mixture comprising butene; the butene purification unit 280 for purifying the butene mixture prepared by the butene preparation unit; and the butene oligomer preparation unit 270 for preparing butene oligomers from the butene mixture prepared by the butene preparation unit, wherein the hydrogen produced by the reaction unit in the electrocatalysis device is supplied to the first hydrogen reaction unit and the second hydrogen reaction unit, and the thermal energy of the electrocatalysis device and the chemical catalysis device is exchanged with each other.

The thermal energy flow in the integrated system 1000 according to the present invention as shown in FIG. 4 is illustrated specifically and will be explained in detail.

The thermal energy required by the reaction unit 110 may be supplied from the removal unit 121 and the butene purification unit 280.

The thermal energy required by the removal unit 121 may be supplied from one or more units of the first hydrolysis unit 210, the first hydrogen reaction unit 220 and the hydrogen reactant purification unit 250.

The thermal energy required by the first hydrolysis unit 210 may be supplied from one or more units of the second purification unit 123 and the hydrogen reactant purification unit 250.

The thermal energy required by the second hydrolysis unit 230 may be supplied from one or more units of the first purification unit 122, the hydrogen reactant purification unit 250, and the butene oligomer preparation unit.

The thermal energy required by the second hydrogen reaction unit 240 may be supplied from the third purification unit 124.

The thermal energy required by the hydrogen reactant purification unit 250 may be supplied from one or more units of the first hydrogen reaction unit 220 and the butene purification unit 280.

In addition, the present invention provides a method comprising:

a step of carrying out an oxidation reaction at the anode by an electrocatalysis of glycerol and at the cathode producing hydrogen through a reduction reaction (step 1-1);

a step of purifying one or more value-added chemicals selected from the group consisting of glyceraldehyde (GAD), hydroxypyruvic acid (HPA), and glyceric acid (GLA) from the reaction products produced through the oxidation reaction at the anode in step 1-1 (step 1-2);

a step of hydrolyzing lignocellulosic biomass to furfural (FF) and levulinic acid (LA) (step 2-1);

a step of subjecting furfural (FF) produced in step 2-1 to a reaction with hydrogen so as to convert to furfuryl alcohol (FFA) (step 2-2);

a step of hydrolyzing furfuryl alcohol (FFA) produced in step 2-2 to levulinic acid (LA) (step 2-3);

a step of subjecting levulinic acid (LA) to a reaction with hydrogen so as to convert to gamma-valerolactone (GVL) (step 2-4); and a step of producing butene oligomers from gamma-valerolactone (GVL) produced in step 2-4 (step 2-5), wherein hydrogen produced in step 1-1 is used for step 2-2 and step 2-4, and the steps exchange the thermal energy with one another.

Hereinafter, a method for operating the integrated system according to the present invention will be described in detail with reference to the schematic diagrams of the integrated system 1000 according to the present invention in FIGS. 1 to 4.

The thermal energy produced in step 1-2 may be supplied to one or more of step 1-1, step 2-1, step 2-3, and step 2-4.

The thermal energy produced in step 2-1 may be supplied to step 1-2.

Step 1-1 or step 1-2 in the method of the present invention may be applied to any method without limitation so long as the method is capable of preparing glycerol derivatives and hydrogen from glycerol. Steps 2-1 to 2-5 may also be applied to any method without limitation so as long the method is capable of preparing butene oligomers from lignocellulosic biomass.

MODE FOR CARRYING OUT THE INVENTION

Hereinafter, a method of the present invention will be described in detail through one example.

In step 1-1, which is for preparing glycerol derivatives and hydrogen, an electrocatalytic reactor may be used as a reactor and Pt/C may be used as a catalyst, but the catalyst is not limited thereto.

First, at the anode, glycerol derivatives comprising one or more of GAD, HPA, and GLA are prepared from glycerol. As a more specific example, 0.1 M to 1.0 M glycerol in 0.1 M to 1.0 M sulfuric acid aqueous solution may be subjected to react by applying the electrode voltage of 0.5 V to 2.0 V under the condition of the temperature ranging from 50° C. to 70° C. and the pressure ranging from 0.5 bar to 2 bar and glycerol may be oxidized at the anode to produce various glycerol derivatives. As for the carbon yield, glycerol derivatives may include 20% to 25% of GAD, 25% to 35% of GLA, 1% to 10% of HPA, and besides, may further comprise tartronic acid (TTA), glycolic acid (GCA), and oxalic acid (OXA). As one example, when about 0.5 M glycerol in 0.5 M sulfuric acid aqueous solution was subjected to react by applying the electrode voltage of 1.1 V under the condition of the temperature of 60° C. and the pressure of 1 bar, the carbon yield for glycerol derivatives may be 23.6% GAD, 31.7% GLA, 6.6% HPA, 1.2% TTA, 3.7% GCA, 0.3% OXA.

In addition, hydrogen is produced at the cathode wherein the molar ratio of glycerol to hydrogen is about 1.0 to 2 times, 1.1 to 1.5 times, and 1.2 to 1.3 times.

Following step 1-1, where sulfuric acid aqueous solution is used, a sulfuric acid neutralization process may be carried out. Specifically, the process may be carried out under the condition of the temperature of 25° C. to 170° C. and the pressure of 1 bar to 16 bar.

Step 1-2 is the step of purifying one or more value-added chemicals of glyceraldehyde (GAD), glyceric acid (GLA), and hydroxypyruvic acid (HPA) from the reaction products produced through the oxidation reaction at the anode in step 1-1, and as a specific example, step 1-2 may be carried out successively in: a step of removing water and impurities from the reaction products produced through the oxidation reaction at the anode; a step of purifying glyceraldehyde (GAD) from the reaction products; a step of purifying hydroxypyruvic acid (HPA) from the reaction products; and a step of purifying glyceric acid (GLA) from the reaction products.

The step of removing water and other impurities may be carried out by a multi-stage distillation apparatus and the multi-stage distillation apparatus may be a continuous multi-stage distillation apparatus having 8 to 12 stages.

The step of purifying glyceraldehyde (GAD) may be carried out by a multi-stage distillation apparatus and the multi-stage distillation apparatus may be a multi-stage distillation apparatus having 10 to 16 stages.

The step of purifying hydroxypyruvic acid (HPA) may be carried out by a multi-stage distillation apparatus and the multi-stage distillation apparatus may be a multi-stage distillation apparatus having 45 to 55 stages.

The step of purifying glyceric acid (GLA) may be carried out by a multi-stage distillation apparatus and the multi-stage distillation apparatus may be a multi-stage distillation apparatus having 35 to 45 stages.

Step 2-1 is the step of hydrolyzing lignocellulosic biomass to furfural (FF) and levulinic acid (LA). In step 2-1, sulfuric acid is used as the catalyst and the concentration of the catalyst may be 0.01 M to 0.5 M or 0.05 M to 0.2 M. As a solvent for hydrolysis, gamma-valerolactone (GVL) may be used in combination with water and lignocellulosic biomass may be used at the concentration of 10% by weight to 20% by weight or 12% by weight to 18% by weight. Hydrolysis may be carried out under the condition of the temperature ranging from 100° C. to 200° C. and the pressure ranging from 10 bar to 20 bar for 30 minutes to 3 hours. Herein, the lignocellulosic biomass may be corn stover, wheat straw, hybrid poplar, switchgrass, loblolly pine, aspen wood, and the like. As one example, where lignocellulosic biomass contained in the mixed solvent of GVL and water at the concentration of 16% by weight is subjected to react by using sulfuric acid at the concentration of 0.1 M as the catalyst under the condition of the temperature of 170° C. and the pressure of 16 bar for 1.5 hours, hemicelluloses may be converted to furfural (FF) with the yield of 56 mol % and celluloses may be converted to levulinic acid (LA) with the yield of 61 mol %.

Step 2-2 is the step of subjecting furfural (FF) to the reaction with hydrogen to convert to furfuryl alcohol (FFA), in which $Pt_3Sn/SiO_2$ may be used as the catalyst. Herein, FF and hydrogen may be supplied to step 2-2 and subjected to react under the condition of the temperature of 150° C. and the pressure of 20 bar to 50 bar. As one example, where FF is subjected to react by using $Pt_3Sn/SiO_2$ as the catalyst under the condition of the temperature of 100° C. and the pressure of 35 bar, FF may be converted to FFA with the yield of about 90 mol %. For the hydrogen in step 2-2, it is preferred to supply the hydrogen produced in step 1-1.

Step 2-3 is the step of hydrolyzing furfuryl alcohol (FFA) to levulinic acid (LA), in which Amberlyst 70 may be used as the catalyst. Herein, FFA may be supplied to step 2-3 and subjected to react under the condition of the temperature of 100° C. to 150° C. and the pressure of 10 bar to 50 bar. As one example, where FFA is subjected to react by using Amberlyst 70 as the catalyst under the condition of the temperature of 125° C. and the pressure of 35 bar, it may be converted to LA with the yield of about 70 mol %.

Step 2-4 is the step of subjecting levulinic acid (LA) to the reaction with hydrogen to convert to gamma-valerolactone (GVL), in which $RuSn_4/C$ may be used as the catalyst. Herein, LA and hydrogen may be supplied to step 2-4 and subjected to react under the condition of the temperature of 200° C. to 250° C. and the pressure of 10 bar to 50 bar. As one example, where LA is subjected to react by using $RuSn_4/C$ as the catalyst under the condition of the temperature of 220° C. and the pressure of 36 bar, LA may be converted to GVL with the yield of about 99 mol %. For the hydrogen in step 2-4, it is preferred to supply the hydrogen produced in step 1-1.

Following step 2-4, carbon dioxide may be excessively contained as an impurity and thus, a carbon dioxide separation step may be further carried out. The carbon dioxide separation step, which is a step of separating carbon dioxide by using a reduced pressure and cooling, may be carried out under the condition of the temperature of 150° C. to 200° C. and the pressure of 5 bar to 15 bar.

In addition, a step of purifying gamma-valerolactone (GVL) produced in step 2-4 may be further comprised in the method. The step of purifying GVL may be carried out by an evaporator under the condition of the temperature of 200° C. to 300° C. and the pressure of 1.0 bar to 2.0 bar.

Step 2-5 is a step of producing butene oligomers from gamma-valerolactone (GVL) and more particularly, it may comprise: a step of producing a butene mixture comprising butene from gamma-valerolactone (GVL); a step of purifying butene from the butene mixture; and a step of preparing butene oligomers from the purified butene.

As one specific example, the step of producing a butene mixture comprising butene from gamma-valerolactone (GVL) may use $SiO_2/Al_2O_3$ as the catalyst. GVL may be supplied to the step of producing the butene mixture and subjected to react under the condition of the temperature of 300° C. to 400° C. and the pressure of 10 bar to 50 bar. As one example, where GVL is subjected to react by using $SiO_2/Al_2O_3$ as the catalyst under the condition of the temperature of 375° C. and the pressure of 36 bar, GVL is converted to butene with the yield of 99 mol %.

The step of purifying butene from the butene mixture may be carried out by a multi-stage distillation apparatus and the multi-stage distillation apparatus may be a multi-stage distillation apparatus having 40 to 45 stages.

The step of preparing butene oligomers from the purified butene may use Amberlyst 70 as the catalyst. Butene may be supplied to the step of preparing the butene oligomers and subjected to react under the condition of the temperature of 120° C. to 250° C. and the pressure of 10 bar to 50 bar. As one example, where butene is subjected to react by using Amberlyst 70 as the catalyst under the condition of the temperature of 170° C. and the pressure of 36 bar, butene is converted to butene oligomers with the yield of 99 mol %.

Accordingly, the process for preparing glycerol derivatives can process 127,000 tons of glycerol per year so as to produce 45,400 tons of glyceric acid (GLA), 28,600 tons of glyceraldehyde (GAD), 8,960 tons of hydroxypyruvic acid (HPA), and 3,560 tons of hydrogen per year and the process for preparing butene oligomers can process 701,000 tons of lignocellulosic biomass per year so as to produce 74,100 tons of butene oligomers per year. In addition, about 56.2% (2,000 tons per year) of the hydrogen produced in the process for preparing glycerol derivatives is used in the process for preparing butene oligomers.

In addition, the method according to the present invention is characterized in that the thermal integration network is constructed so as that heat exchange is carried out in each step.

Hereinafter, the present invention will be described in detail through the following experimental example.

However, the following experimental example is only illustrative of the present invention and the scope of the invention is not limited by the experimental example.

EXPERIMENTAL EXAMPLE

First, this experiment was based on the production of 45,400 tons of glyceric acid (GLA) per year among glycerol derivatives, and each energy was calculated through the higher heating value (HHV). The energy content of glycerol is 73.2 MW; the energy content of hydrogen ($H_2$) is 16.8 MW; the energy contents of glyceric acid (GLA), hydroxypyruvic acid (HPA), and glyceraldehyde (GAD) are 15.1 MW, 2.2 MW, and 13.7 MW, respectively. The energy content of other byproducts is 17.0 MW.

Figure 5:
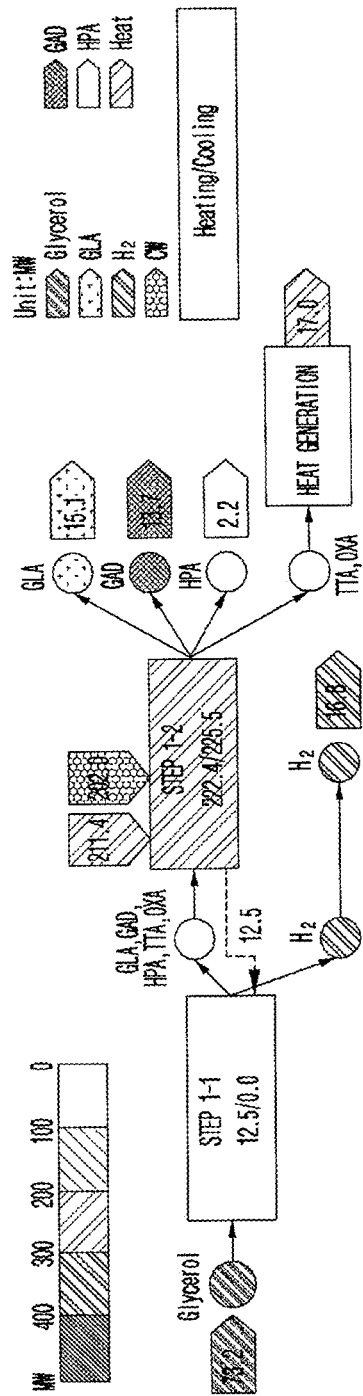
FIG. 5 is an energy flow chart concerning a single process for preparing glycerol derivatives.

The energy flow chart concerning the thermal integration network of a single preparation process for preparing glycerol derivatives is shown in FIG. 5.

In the step of producing glycerol derivatives and hydrogen through electrocatalysis of glycerol in step 1-1, as a process requiring the thermal energy, there is a heating process of heating up to the reaction temperature (60° C.) and the heating process requires the energy of 12.5 MW. This energy can be supplied fully from the waste heat of a condenser in the multi-stage distillation apparatus (100° C.) and a condensing apparatus (100° C.) in the step of removing water and impurities from the reaction products produced through the oxidation reaction at the anode among the detailed steps in step 1-2.

A reboiler (101° C.) in the multi-stage distillation apparatus in the step of removing water and impurities from the reaction products produced through the oxidation reaction at the anode among the detailed steps in step 1-2 requires the thermal energy of 211.2 MW. This energy can be supplied partly from the waste heat (11.0 MW) of condensers (201° C., 256° C., and 268° C., respectively) in the step of purifying glyceraldehyde, the step of purifying hydroxypyruvic acid, and the step of purifying glyceric acid among the detailed steps in step 1-2.

Accordingly, 23.5 MW of heat can be recovered through the construction of the thermal integration network in the single preparation process for preparing glycerol derivatives and the total thermal energy required for the process is reduced by 10% from 234.9 MW to 211.4 MW.

Next, this experiment was based on the production of 45,400 tons of glyceric acid (GLA) per year among glycerol derivatives, and each energy was calculated through the higher heating value (HHV). The energy content of glycerol is 73.2 MW; the energy content of hydrogen ($H_2$) is 7.4 MW; the energy contents of glyceric acid (GLA), hydroxypyruvic acid (HPA), and glyceraldehyde (GAD) are 15.1 MW, 2.2 MW, and 13.7 MW, respectively.

In addition, the energy content of corn stover, which is lignocellulosic biomass, is 358.0 MW; the energy content of butene oligomers is 115.0 MW; and the total energy content of other byproducts is 159.1 MW.

Figure 6:
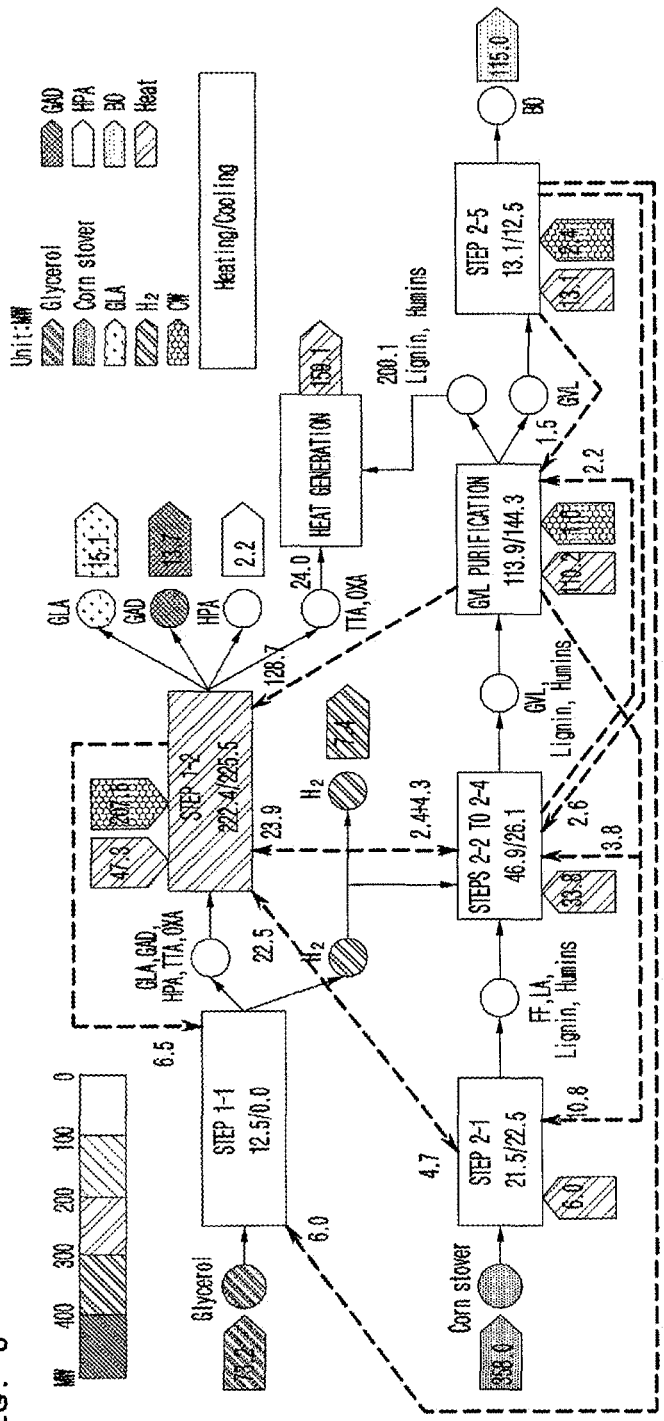
FIG. 6 is an energy flow chart concerning a thermal integration network of a method according to the present invention.

The energy flow chart concerning the thermal integration network of the integrated process of the process for preparing glycerol derivatives and the process for preparing butene oligomers is shown in FIG. 6.

In step 1-1, as a process requiring the thermal energy, there is a heating process of heating up to the reaction temperature (about 60° C.) and the heating process requires the energy of about 12.5 MW. This energy can be supplied fully from the waste heat (about 6.5 MW) in the purification step in step 1-2 or the step of removing water and impurities from the reaction products, which is among the detailed steps in step 1-2, and the waste heat (about 6.0 MW) in the butene production step in step 2-5 or the step of purifying butene from the butene mixture, which is among the detailed steps in step 2-5.

In the step of removing water and impurities from the reaction products produced through the oxidation reaction at the anode among the detailed steps in step 1-2, the thermal energy is required, and particularly a reboiler (102° C.) in the multi-stage distillation apparatus may require 211.2 MW as the thermal energy. This energy can be supplied from the thermal energy generated from the hydrolysis reaction in step 2-1 (about 22.5 MW), the thermal energy generated from the hydrogen reaction in step 2-2 (about 23.9 MW), and the thermal energy generated by the hydrogen reactant purification unit in the step of purifying GVL (about 128.7 MW).

In step 2-1, there is a heating process of heating up to the reaction temperature (about 170° C.) for hydrolysis and the heating process requires the thermal energy of about 21.5 MW. This energy can be supplied partly from the thermal energy generated in the step of purifying hydroxypyruvic acid among the detailed steps in step 1-2 (about 4.7 MW) and the thermal energy generated by the hydrogen reactant purification unit in the step of purifying GVL (about 10.8 MW).

In step 2-3, there is a heating process of heating up to the reaction temperature (125° C.) for hydrolysis and the heating process requires the thermal energy of about 8.7 MW. This energy can be supplied fully from the waste heat (2.4 MW) generated in the step of purifying glyceraldehyde, which is among the detailed steps in step 1-2, the waste heat (3.8 MW) generated by the hydrogen reactant purification unit in the step of purifying GVL, and the heat, of reaction (2.6 MW) generated in the step of preparing butene oligomers, which is among the detailed steps in step 2-5.

In step 2-4, there is a heating process of heating up to the reaction temperature (220° C.) for the reaction with hydrogen and the heating process requires the thermal energy of about 38.1 MW. This energy can be supplied partly from the waste heat generated in the step of purifying glyceric acid, which is among the detailed steps in step 1-2 (4.3 MW).

In the step of purifying gamma-valerolactone (GVL) produced in step 2-4, the thermal energy (11.3 MW) required in the heating process (178° C.) can be supplied partly from the waste heat generated from the hydrogen reaction in step 2-2 (2.2 MW) and the waste heat generated by the condenser in the multi-stage distillation apparatus in the step of purifying butene (1.5 MW).

Accordingly, 219.9 MW of heat can be recovered through the construction of the thermal integration network in the integrated process for preparing glycerol derivatives and butene oligomers and the total thermal energy required for the process is reduced by 51.1% from 430.3 MW to 210.4 MW.

While particular parts of the present invention have been described in detail, it will be apparent to those skilled in the art that this specific description is merely preferred aspects and that the scope of the invention is not limited thereto. Accordingly, it is intended that the actual scope of the present invention is defined by the appended claims and their equivalents.

INDUSTRIAL APPLICABILITY

The integrated system according to the present invention can reduce the cost of materials of a process for preparing butene oligomers by using hydrogen, which is a byproduct of a process for preparing glycerol derivatives, as a material of a process for preparing butene oligomers through the integration of materials and energy from the processes for preparing glycerol derivatives and butene oligomers, and can obtain an effect of reducing energy costs by greatly reducing energy required in an integrated process by supplying, as a part of the thermal energy required at the process for preparing glycerol derivatives, the waste heat of the process for preparing butene oligomers through the construction of a thermal energy integration network.

EXPLANATION OF REFERENCE NUMERALS

1000: Integrated system
100: Electrocatalysis device
110: Reaction unit
120: Purification unit
121: Removal unit
122: First purification unit
123: Second purification unit
124: Third purification unit
200: Chemical catalysis device
210: First hydrolysis unit
220: First hydrogen reaction unit
230: Second hydrolysis unit
240: Second hydrogen reaction unit
250: Hydrogen reactant purification unit
260: Butene preparation unit
270: Butene oligomer preparation unit
280: Butene purification unit

The invention claimed is:

1. An integrated system, comprising:
(a) an electrocatalysis device, in which an oxidation reaction is carried out by an electrocatalysis of glycerol, and hydrogen is produced through a reduction reaction;
(b) a chemical catalysis device for producing butene oligomers from lignocellulosic biomass through a hydrogenation process,
(c) wherein the hydrogen produced by the electrocatalysis device is used for the production of the butene oligomers by the chemical catalysis device;
(d) wherein the electrocatalysis device comprises:
  (i) a reaction unit which comprises an anode, a cathode, and an electrolyte; and
  (ii) a purification unit for purifying reaction products produced by the reaction unit of the electrocatalysis device;
  (iii) equipment for extracting excess thermal energy waste heat from a purification step conducted in the purification unit;
(e) wherein the chemical catalysis device comprises:
  (i) a first hydrolysis unit for hydrolyzing lignocellulosic biomass so as to produce furfural (FF) and levulinic acid (LA);
  (ii) a first hydrogen reaction unit for subjecting furfural (FF) produced by the first hydrolysis unit to a reaction with hydrogen so as to produce to furfuryl alcohol (FFA);
  (iii) a second hydrolysis unit for hydrolyzing furfuryl alcohol (FFA) produced by the first hydrogen reaction unit so as to produce a levulinic acid (LA);
  (iv) a second hydrogen reaction unit for subjecting levulinic acid (LA) produced by the second hydrolysis unit to a reaction with hydrogen so as to produce gamma-valerolactone (GVL);
  (v) a hydrogen reactant purification unit for purifying the gamma-valerolactone (GVL) produced by the second hydrogen reaction unit;
  (vi) a butene preparation unit for catalyzing the gamma-valerolactone (GVL) purified by the hydrogen reactant purification unit so as to prepare a butene mixture comprising butene;
  (vii) a butene purification unit for purifying the butene mixture prepared by the butene preparation unit;
  (viii) a butene oligomer preparation unit for preparing butene oligomers from the butene purified by the butene preparation unit; and
  (ix) equipment for extracting excess thermal energy waste heat from a reaction step conducted in the first and second hydrolysis units, first and second hydrogen reaction units, the hydrogen reactant purification unit, the butene preparation unit, the butene purification unit and the butene prenaration unit; and
(f) wherein at least part of a thermal energy of the reaction unit of the electrocatalysis device is supplied from the excess thermal energy waste heat extracted from the purification unit of the electrocatalysis device or the butene oligomer purification unit of the chemical catalysis device;

(g) wherein at least part of a thermal energy of the first hydrolysis unit of the chemical catalysis device is supplied from the excess thermal energy waste heat extracted from the purification unit of the electrocatalysis device and the hydrogen reactant purification unit of the chemical catalysis device;

(h) wherein at least part of a thermal energy of the second hydrolysis unit of the chemical catalysis device is supplied from the excess thermal energy waste heat extracted from the purification unit of the electrocatalysis device and the hydrogen reactant purification unit and the butene oligomer preparation unit of the chemical catalysis device;

(i) wherein at least part of a thermal energy of the second hydrogen reaction unit of the chemical catalysis device is supplied from the excess thermal energy waste heat extracted from the purification unit of the electrocatalysis device and the hydrogen reactant purification of the chemical catalysis device;

(j) wherein at least part of a thermal energy of the hydrogen reactant purification unit of the chemical catalysis device is supplied from the excess thermal energy waste heat extracted from the first hydrogen reaction unit and the butene purification unit of the chemical catalysis device; and (k) wherein at least part of a thermal energy for the purification unit of the electrocatalysis device is supplied from excess thermal energy waste heat extracted from the first hydrolysis unit, the first hydrogen reaction unit, or the hydrogen reactant purification unit.

2. The integrated system of claim 1, wherein the purification unit comprises:

(a) a removal unit for removing water and other impurities from the reaction products;

(b) a first purification unit for purifying glyceraldehyde (GAD) from the reaction products;

(c) a second purification unit for purifying hydroxypyruvic acid (HPA) from the reaction products; and (d) a third purification unit for purifying glyceric acid (GLA) from the reaction products.

3. The integrated system of claim 1:

(a) wherein the oxidation reaction is carried out at the anode by an electrocatalysis of glycerol, and hydrogen is produced through a reduction reaction at the cathode; and (b) wherein the hydrogen produced by the reaction unit in the electrocatalysis device is supplied to the first hydrogen reaction unit and the second hydrogen reaction unit, and is used in the production of butane oligomers.

4. A method of operating the integrated system of claim 1, comprising:

(a) a step 1-1 of carrying out an oxidation reaction by an electrocatalysis of glycerol and producing hydrogen through a reduction reaction;

(b) a step 1-2 of purifying one or more value-added chemicals selected from the group consisting of glyceraldehyde (GAD), hydroxypyruvic acid (HPA), and glyceric acid (GLA) from the reaction products produced through the oxidation reaction at the anode in step (a);

(c) a step 2-1 of hydrolyzing lignocellulosic biomass to furfural (FF) and levulinic acid (LA);

(d) a step 2-2 of subjecting furfural (FF) produced in step 2-1 to a reaction with hydrogen so as to convert to furfuryl alcohol (FFA);

(e) a step 2-3 of hydrolyzing furfuryl alcohol (FFA) produced in step (d) to levulinic acid (LA);

(f) a step 2-4 of subjecting levulinic acid (LA) to a reaction with hydrogen so as to convert to gamma-valerolactone (GVL); and (g) a step 2-5 of producing butene oligomers from gamma-valerolactone (GVL) produced in step (f);

(h) wherein steps 1-1 and 1-2 are carried out in the electrocatalysis device;

(i) wherein steps 2-1 to 2-5 are carried out in the chemical catalysis device; and (j) wherein hydrogen produced in step 1-1 is used for step 2-2 and step 2-4, and the steps exchange a thermal energy with one another.

5. The method of claim 4, wherein step 1-2 is carried out successively in:

(i) a step of removing water and impurities from the reaction products produced through the oxidation reaction at the anode;

(ii) a step of purifying glyceraldehyde (GAD) from the reaction products;

(iii) a step of purifying hydroxypyruvic acid (HPA) from the reaction products; and (iv) a step of purifying glyceric acid (GLA) from the reaction products.

6. The method of claim 4, wherein a thermal energy generated in step 1-2 is supplied to one or more steps selected from the group consisting of step 1-1, step 2-1, step 2-3, and step 2-4.

7. The method of claim 4, wherein a thermal energy generated in step 2-1 is supplied to step 1-2.

* * * * *